United States Patent [19]

Sinskey et al.

[11] Patent Number: 5,641,660
[45] Date of Patent: Jun. 24, 1997

[54] GLUTAMICUM THREONINE BIOSYNTHETIC PATHWAY

[75] Inventors: Anthony J. Sinskey, Boston; Maximillian T. Follettie, Cambridge, both of Mass.; Wolfgang Liebl, Eching, Germany; Oliver P. Peoples, Arlington, Mass.

[73] Assignee: Massachusetts Institute of Technology, Cambridge, Mass.

[21] Appl. No.: 503,325

[22] Filed: Apr. 2, 1990

Related U.S. Application Data

[63] Continuation of Ser. No. 62,552, Jun. 12, 1987, abandoned.

[51] Int. Cl.⁶ .............................. C12P 13/08; C12N 15/67
[52] U.S. Cl. .................. 435/115; 435/172.1; 435/172.3; 435/183; 435/252.32; 435/320.1; 536/23.2; 536/23.7; 536/24.1
[58] Field of Search ...................... 435/69.1, 71.2, 435/115, 172.1, 172.3, 252.3, 252.32, 320.1, 843, 183, 320.2; 536/27, 23.2, 23.7, 24.1; 935/6, 8, 9, 10, 22, 27, 29, 33, 38, 39, 40, 44, 45, 59, 60, 61, 66, 72

[56] References Cited

U.S. PATENT DOCUMENTS

4,894,331 1/1990 Ratzkin et al. ........................ 435/94

OTHER PUBLICATIONS

Sano et al, 1986, *Chemical Abstracts*, 105(9): 532; Abstract No. 77571f.
Nakamori et al., 1985, *Chemical Abstracts*, 102(15): 499; Abstract No. 130461m.
Nakamori et al., 1985, *Chemical Abstracts*, 102(25): 188; Abstract No. 216318g.
Parsot et al., 1983, *NAR*, vol. 11(2): 7331–7345.
Cossart et al., 1981, *NAR*, vol. 9(2): 339–347.
Warburton et al, 1983, *NAR*, vol 11(17): 5837–5854.
Miwa et al., 1984, *Agric Biol. Chem*, 48(9): 2233–2237.
Nakamori et al, 1987 (Jan.), *Agric Biol Chem.*, 51(1): 87–91.
Morinaga et al., 1987 (Jan.), *Agric Biol. Chem.*, 51(1): 93–100.
Takagi et al., 1987 (Feb.), *Chemical Abstracts*, vol. 105(7): Abstract No. 48643w.
Mateos et al., 1987 (May), *NAR*, 15(9): 3922.
Sinskey et al. Eur. Congr. Biotechnol. 3:35 (1987) Abstract Only.
Mateos et al. Mar. (1987) Mol. Gen. Genet 206:361–367.

*Primary Examiner*—John L. LeGuyader
*Attorney, Agent, or Firm*—Arnall Golden & Gregory

[57] ABSTRACT

The present invention is a method for the isolation and characterization of *C. glutamicum* genes involved in amino acid biosynthesis, specifically, encoding hom, thrB, and thrC, and sequences regulating their expression. Techniques for modifying or replacing these sequences and means for facilitating further isolations and characterizations, including promoter probe vectors which are useful in screening for high efficiency and regulatable promoters and repressors, are also disclosed.

A *C. glutamicum* genomic library was constructed by cleaving chromosomal DNA with restriction enzymes, inserting the DNA fragments into an appropriate vector, and transforming the resulting recombinant molecules (rDNA) into *C. glutamicum*. Amino acid biosynthetic genes hom, thrB, and thrC, encoding homoserine dehydrogenase, homoserine kinase, and threonine synthetase, respectively, were isolated by complementation of *C. glutamicum* auxotrophs. The hom-thrB genes were subcloned on a 3.6 kb Sal1 generated chromosomal fragment while thrC activity was isolated from a second recombinant plasmid within the genomic library and subcloned on a 2.7 kb Sph1 generated fragment. The hom-thrB and thrC loci, and regulatory sequences, were identified by enzyme assays, complementation of defined *E. coli* auxotrophs, S1 nuclease and deletion mapping.

16 Claims, 13 Drawing Sheets

FIGURE 3A

The Nucleotide Sequence and Predicted Protein Sequences of homA and thrB.

```
   1 GTCGACCGCGTGAAGTCGCCCTTTAGGAGAATTCTGACTAACTGGAGCCAAAACTTGATC   60
  61 CACTCGAGAGCTGTGCAGTCTCTTTTTCCTTCAATTCTGCCTGCTCGAGCTCGTAGAAGT  120
 121 AGAGGTCTACTTCAGTTGGTTCACCTTGCACACAAGCATGAAGTAGTGGGTAGGTCGAGT  180
 181 TGTTAAATGCGGTGTAGAAGGGGAGTAGTTCGCTAGCAAAGGTTAATTTGGAGTCGCTGT  240
 241 ACTGCGGGTTCTCGGGTGGAGTATTCCCGGAGGATTCAAGAAATCTTGACGCATCTTTGA  300
 301 TGAGGTATGTTTGGAATTCGTCGGCACCTTCCTCGCCGGAGAGGTAGTAGGAGTTGTCGT  360
 361 AATTTGGAACCCAGATGGCAAATCGTGCGTTTTCGATTGCGTCCAGGACTTCCTCTACGT  420
 421 TGTATCTCGCACTTGTTGCAGCGGAAGCGACTCGGTTGCCGATGTCTCCGTATGCAGTGA  480
 481 GCGTGGCGTTTCCGAGGGGAACTTGATCAGAGGAATACACCATGGAGCCGATGTCAGAGG  540
 541 CGACTGCGGGCAGATCCTTTTGAAGCTGTTTCACAATTTCTTTGCCCAGTTCGCGGCGGA  600
 601 TCTGGAACCACTTTTGCATGCGATCGTCGTCAGAGTGGTTCATGTGAAAAATACACTCAC  660
 661 CATCTCAATGGTCATGGTGAAGGCCTGTACTGGCTGCGACAGCATGGAACTCAGTGCAAT  720
 721 GGCTGTAAGGCCTGCACCAACAATGATTGAGCGAAGCTCCAAAATGTCCTCCCCGGGTTG  780
 781 ATATTAGATTTCATAAATATACTAAAAATCTTGAGAGTTTTTCCGTTGAAAACTAAAAAG  840
 841 CTGGGAAGGTGAATCGAATTTCGGGGCTTTAAAGCAAAAATGAACAGCTTGGTCTATAGT  900
 901 GGCTAGGTACCCTTTTTGTTTTGCACACATGTAGGGTGGCCGAAACAAAGTAATAFFACA  961
```

```
                                              MetThrSerAlaSerAlaProSerPhe
 961 ACAACGCTCGACCGCGATTATTTTTGGAGAATCATGACCTCAGCATCTGCCCCAAGCTTT 1020
                                              Translation Initiation Codon
```

```
     AsnProGlyLysGlyProGlySerAlaValGlyIleAlaLeuLeuGlyPheGlyThrVal
1021 AACCCCGGCAAGGGTCCCGGCTCAGCAGTCGGAATTGCCCTTTTAGGATTCGGAACAGTC 1080
```

FIGURE 3B

```
          GlyThrGluValMetArgLeuMetThrGluTyrGlyAspGluLeuAlaHisArgIleGly
1081 GGCACTGAGGTGATGCGTCTGATGACCGAGTACGGTGATGAACTTGCGCACCGCATTGGT 1140

GlyProLeuGluValArgGlyIleAlaValSerAspIleSerLysProArgGluGlyVal
1141 GGCCCACTGGAGGTTCGTGGCATTGCTGTTTCTGATATCTCAAAGCCACGTGAAGGCGTT 1200

AlaProGluLeuLeuThrGluAspAlaPheAlaLeuIleGluArgGluAspValAspIle
1201 GCACCTGAGCTGCTCACTGAGGACGCTTTTGCACTCATCGAGCGCGAGGATGTTGACATC 1260

ValValGluValIleGlyGlyIleGluTyrProArgGluValValLeuAlaAlaLeuLys
1261 GTCGTTGAGGTTATCGGCGGCATTGAGTACCCACGTGAGGTAGTTCTCGCAGCTCTGAAG 1320

AlaGlyLysSerValValThrAlaAsnLysAlaLeuValAlaAlaHisSerAlaGluLeu
1321 GCCGGCAAGTCTGTTGTTACCGCCAATAAGGCTCTTGTTGCAGCTCACTCTGCTGAGCTT 1380

AlaAspAlaAlaGluAlaAlaAsnValAspLeuTyrPheGluAlaAlaValAlaGlyAla
1381 GCTGATGCAGCGGAAGCCGCAAACGTTGACCTGTACTTCGAGGCTGCTGTTGCAGGCGCA 1440

IleProValValGlyProLeuArgArgSerLeuAlaGlyAspGlnIleGlnSerValMet
1441 ATTCCAGTGGTTGGCCCACTGCGTCGCTCCCTGGCTGGCGATCAGATCCAGTCTGTGATG 1500

GlyIleValAsnGlyThrThrAsnPheIleLeuAspAlaMetAspSerThrGlyAlaAsp
1501 GGCATCGTTAACGGCACCACCAACTTCATCTTGGACGCCATGGATTCCACCGGCGCTGAC 1560

TyrAlaAspSerLeuAlaGluAlaThrArgLeuGlyTyrAlaGluAlaAspProThrAla
1561 TATGCAGATTCTTTGGCTGAGGCAACTCGTTTGGGTTACGCCGAAGCTGATCCAACTGCA 1620

AspValGluGlyHisAspAlaAlaSerLysAlaAlaIleLeuAlaSerIleAlaPheHis
1621 GACGTCGAAGGCCATGACGCCGCATCCAAGGCTGCAATTTTGGCATCCATCGCTTTCCAC 1680

ThrArgValThrAlaAspAspValTyrCysGluGlyIleSerAsnIleSerAlaAlaAsp
1681 ACCCGTGTTACCGCGGATGATGTGTACTGCGAAGGTATCAGCAACATCAGCGCTGCCGAC 1740

IleGluAlaAlaGlnGlnAlaGlyHisThrIleLysLeuLeuAlaIleCysGluLysPhe
1741 ATTGAGGCAGCACAGCAGGCAGGCCACACCATCAAGTTGTTGGCCATCTGTGAGAAGTTC 1800

ThrAsnLysGluGlyLysSerAlaIleSerAlaArgValHisProThrLeuLeuProVal
1801 ACCAACAAGGAAGGAAAGTCGGCTATTTCTGCTCGCGTGCACCCGACTCTATTACCTGTG 1860

SerHisProLeuAlaSerValAsnLysSerPheAsnAlaIlePheValGluAlaGluAla
1861 TCCCACCCACTGGCGTCGGTAAACAAGTCCTTTAATGCAATCTTTGTTGAAGCAGAAGCA 1920

AlaGlyArgLeuMetPheTyrGlyAsnGlyAlaGlyGlyAlaProThrAlaSerAlaVal
1921 GCTGGTCGCCTGATGTTCTACGGAAACGGTGCAGGTGGCGCGCCAACCGCGTCTGCTGTC 1980

LeuGlyAspValValGlyAlaAlaArgAsnLysValHisGlyGlyArgAlaProGlyGlu
1981 CTTGGCGACGTCGTTGGTGCCGCACGAAACAAGGTGCACGGTGGCCCTGCTCCAGGTGAG 2040
```

FIGURE 3C

```
         SerThrTyrAlaAsnLeuProIleAlaAspPheGlyGluThrThrThrArgTyrHisLeu
2041 TCCACCTACGCTAACCTGCCGATCGCTGATTTCGGTGAGACCACCACTCGTTACCACCTC 2100

AspMetAspValGluAspArgValGlyValLeuAlaGluLeuAlaSerLeuPheSerGlu
2101 GACATGGATGTGGAAGATCGCGTGGGGGTTTTGGCTGAATTGGCTAGCCTGTTCTCTGAG 2160

GlnGlyIleSerLeuArgThrIleArgGlnGluGluArgAspAspAspAlaArgLeuIle
2161 CAAGGAATCTCCCTGCGTACAATCCGACAGGAAGAGCGCGATGATGATGCACGTCTGATC 2220

ValValThrHisSerAlaLeuGluSerAspLeuSerArgThrValGluLeuLeuLysAla
2221 GTGGTCACCCACTCTGCGCTGGAATCTGATCTTTCCCGCACCGTTGAACTGCTGAAGGCT 2280

LysProValValLysAlaIleAsnSerValIleArgLeuGluArgAsp
2281 AAGCCTGTTGTTAAGGCAATCAACAGTGTGATCCGCCTCGAAAGGGACTAATTTTACTGA 2340
                                                         Stop Predicated start of thrB translation
         MetAlaIleGluLeuAsnValGlyArgLysValThrValThrValProGlySerSerAl
2341 CATGGCAATTGAACTGAACGTCGGTCGTAAGGTTACCGTCACGGTACCTGGATCTTCTGC 2400
         Translation initiation Codon aAsnLeuGlyProGlyPheAspThrLeuGlyLeuAlaLeuSerValTyrAspThrValGl
2401 AAACCTCGGACCTGGCTTTGACACTTTAGGTTTGGCACTGTCGGTATACGACACTGTCGA 2460 uValGluIleIleProSerGlyLeuGluValGluValPheGlyGluGlyGlnGlyGluVa
2461 AGTGGAAATTATTCCATCTGGCTTGGAAGTGGAAGTTTTTGGCGAAGGCCAAGGCGAAGT 2520

LProLeuAspGlySerHisLeuValValLysAlaIleArgAlaGlyLeuLysAlaAlaAs
2521 CCCTCTTGATGGCTCCCACCTGGTGGTTAAAGCTATTCGTGCTGGCCTGAAGGCAGCTGA 2580 pAlaGluValProGlyLeuArgValValCysHisAsnAsnIleProGlnSerArgGlyLe
2581 CGCTGAAGTTCCTGGATTGCGAGTGGTGTGCCACAACAACATTCCGCAGTCTCGTGGTCT 2640

UGlySerSerAlaAlaAlaAlaValAlaGlyValAlaAlaAlaAsnGlyLeuAlaAspPh
2641 TGGCTCCTCTGCTGCAGCGGCGGTTGCTGGTGTTGCTGCAGCTAATGGTTTGGCGGATTT 2700

EProLeuThrGlnGluGlnIleValGlnLeuSerSerAlaPheGluGlyHisProAspAs
2701 CCCGCTGACTCAAGAGCAGATTGTTCAGTTGTCCTCTGCCTTTGAAGGCCACCCAGATAA 2760 nAlaAlaAlaSerValLeuGlyGlyAlaValValSerTrpThrAsnLeuSerIleAspGl
2761 TGCTGCGGCTTCTGTGCTGGGTGGAGCAGTGGTGTCGTGGACAAATCTGTCTATCGACGG 2820 yLysSerGlnProGlnTyrAlaAlaValProLeuGluValGlnAspAsnIleArgAlaTh
2821 CAAGAGCCAGCCACAGTATGCTGCTGTACCACTTGAGGTGCAGGACAATATTCGTGCGAC 2880 rAlaLeuValProAsnPheHisAlaSerThrGluAlaValArgArgValLeuProThrGl
2881 TGCGCTGGTTCCTAATTTCCACGCATCCACCGAAGCTGTGCGCCGAGTCCTTCCCACTGA 2940 uValThrHisIleAspAlaArgPheAsnValSerArgValAlaValMetIleValAlaLe
2941 AGTCACTCACATCGATGCGCGATTTAACGTGTCCCGCGTTGCAGTGATGATCGTTGCGTT 3000
```

FIGURE 3D

```
       uGlnGlnArgProAspLeuLeuTrpGluGlyThrArgAspArgLeuHisGlnProTyrAr
3001   GCAGCAGCGTCCTGATTTGCTGTGGGAGGGTACTCGTGACCGTCTGCACCAGCCTTATCG 3060 gAlaGluValLeuProIleThrSerGluTrpValAsnArgLeuArgAsnArgGlyTyrAl
3061   TGCAGAAGTGTTGCCTATTACCTCTGAGTGGGTAAACCGCCTGCGCAACCGTGGCTACGC 3120 aAlaTyrLeuSerGlyAlaGlyProThrAlaMetValLeuSerThrGluProIleProAs
3121   GGCATACCTTTCCGGTGCCGGCCCAACCGCCATGGTGCTGTCCACTGAGCCAATTCCAGA 3180 pLysValLeuGluAspAlaArgGluSerGlyIleLysValLeuGluLeuGluValAlaGl
3181   CAAGGTTTTGGAAGATGCTCGTGAGTCTGGCATTAAGGTGCTTGAGCTTGAGGTTGCGGC 3240

YProValLysValGluValAsnGlnPro
3241   ACCAGTCAAGGTTGAAGTTAACCAACCTTAGGCCCAACAAGGAAGGCCCCTTCGAATCAA 3300
                                    Stop         Computer predicted 3301   GAAGGGGCCTTATTAGTGCAGCAATTATTCGCTGAACACGTGAACCTTACAGGTGCCCGG 3360
       translation intermination point

3361   CGCGTTGAGTGGTTTGAGTTCCAGCTGGATGCGGTTGTTTTCACCGAGGCTTTCTTGGAT 3420

3421   GAATCCGGCGTGGATGGCGCAGACGAAGGCTGATGGGCGTTTGTCGTTGACCACAAATGG 3480

3481   GCAGCTGTGTAGAGCGAGGGAGTTTGCTTCTTCGGTTTCGGTGGGGTCAAAGCCCATTTC 3540

3541   GCGGAGGCGGTTAATGAGCGGGGAGAGGGCTTCGTCGAGTTCTTCGGCTTCGGCGTGGTT 3600

3601   AATGCCCATGACGTGTGCCCACTGGGTTCCGATGGAAAGTGCTTTGGCGCGGAGGTCGGG 3660

3661   GTTGTTGCATTGCGTCATCGTCGAC                                    3685
```

FIGURE 4A

The Nucleotide Sequence and Predicted Protein Sequence of thrC gen DNA
Length: 3146  Check: 9461

```
  1  TGACCGAGAGTTTTTTTGAGCAACTGGATCATTAGATAATTGTTCGATCGACCGAATGAA   60

61  ATCACCCGTTATGGAGACCTACTGGAATTGAGCCCAGAAACCGTCGATGTGTGCCTCAAC  120

121  GTAGGGGTAAAGCCACGGCCCGAGCAGCACCAGCCCGACCGCGAGCACCGAACAACCAAT  180

181  GAGAACATACAGGTTCCACTTGGACACCGGCGCTGGATTAAGGATTTCAACTGCGGTGAG  240

241  ATTCTTCTTGTTGTTGTCCTCGAGTTTCGAGAAGCTGGGGTAATCGGGAGCTGTCATCTT  300

301  TAAAGCACATCCTAAAACCGACAATTGAAAGTGATCAGCAACACTTTAGGGTATCGCGTG  360
```

Predicted start of thrC translation

```
                                            ValGlyGluTyrCysValThrProT
361  GGCGAAGTCACCTTTTTCAACATATTTGAGACGGTGTGGGGGAGTATTGTGTCACCCCTT  420
                    ribosome binding sequence rpIleGlyLeuTyrProTrpThrThrPheArgProArgAspAlaSerArgThrProAlaA
421  GGATAGGGTTATATCCGTGGACTACATTTCGACCGCGTGATGCCAGCCGTACCCCTGCCC  480 rgPheSerAspIleLeuLeuGlyGlyLeuAlaProAspGlyGlyLeuTyrLeuProAlaT
481  GCTTCAGTGATATTTTGCTGGGCGGTCTAGCACCAGACGGCGGCCTGTACCTGCCTGCAA  540 hrTyrProGlnLeuAspAspAlaGlnLeuSerLysTrpArgGluValLeuAlaAsnGluG
541  CCTACCCTCAACTAGATGATGCCCAGCTGAGTAAATGGCGTGAGGTATTAGCCAACGAAG  600 lyTyrAlaAlaLeuAlaArgGluValIleSerLeuPheValAspAspIleProValGluA
601  GATACGCAGCTTTGGCTCGTGAAGTTATCTCCCTGTTTGTTGATGACATCCCAGTAGAAG  660 spIleLysAlaIleThrAlaArgAlaTyrThrTyrProLysPheAsnSerGluAspIleV
661  ACATCAAGGCGATCACCGCACGCGCCTACACCTACCCGAAGTTCAACAGCGAAGACATCG  720 alProValThrGluLeuGluAspAsnIleTyrLeuGlyHisLeuSerGluGlyProThrA
721  TTCCTGTCACCGAACTCGAGGACAACATTTACCTGGGCCACCTTTCCGAACCCGCAACCG  780 laAlaPheLysAspMetAlaMetGlnLeuLeuGlyGluLeuPheGluTyrGluLeuArgA
781  CTGCATTCAAAGACATGGCCATGCAGCTGCTCGGCGAACTTTTCGAATACGAGCTTCGCC  840 rgArgAsnGluThrIleAsnIleLeuGlyAlaThrSerGlyAspThrGlySerSerAlaG
841  GCCGCAACGAAACCATCAACATCCTGGGCGCTACCTCTGGCGATACCGGCTCCTCTGCGG  900
```

FIGURE 4B

```
     luTyrAlaMetArgGlyArgGluGlyIleArgValPheMetLeuThrProAlaGlyArgM
 901 AATACGCCATGCGCGGCCGCGAGGGAATCCGCGTATTCATGCTGACCCCAGCTGGCCGCA  960 etThrProPheGlnGlnAlaGlnMetPheGlyLeuAspAspProAsnIlePheAsnIleA
 961 TGACCCCATTCCAGCAAGCACAGATGTTTGGCCTTGACGATCCAAACATCTTCAACATCG 1020 laLeuAspGlyValPheAspAspCysGlnAspValValLysAlaValSerAlaAspAlaG
1021 CCCTCGACGGCGTTTTCGACGATTGCCAAGACGTAGTCAAGGCTGTCTCCGCCGACGCAG 1080 luPheLysLysAspAsnArgIleGlyAlaValAsnSerIleAsnTrpAlaArgLeuMetA
1081 AATTCAAAAAGACAACCGCATCGGTGCCGTGAACTCCATCAACTGGGCACGCCTTATGG  1140 laGlnValValTyrTyrValSerSerTrpIleArgThrThrThrSerAsnAspGlnLysV
1141 CACAGGTTGTGTACTACGTTTCCTCATGGATCCGCACCACAACCAGCAATGACCAAAAGG 1230 alSerPheSerValProThrGlyAsnPheGlyAspIleCysAlaGlyHisIleAlaArgG
1201 TCAGCTTCTCCGTACCAACCGGCAACTTCGGTGACATTTGCGCAGGCCACATCGCCCGCC 1260 lnMetGlyLeuProIleAspArgLeuIleValAlaThrAsnGluAsnAspValLeuAspG
1261 AAATGGGACTTCCCATCGATCGCCTCATCGTGGCCACCAACGAAAACGATGTGCTCGACG 1320 luPhePheArgThrGlyAspTyrArgValArgSerSerAlaAspThrHisGluThrSerS
1321 AGTTCTTCCGTACCGGCGACTACCGAGTCCGCAGCTCCGCAGACACCCACGAGACCTCCT 1380 erProSerMetAspIleSerArgAlaSerAsnPheGluArgPheIlePheAspLeuLeuG
1381 CACCTTCGATGGATATCTCCCGCGCCTCCAACTTCGAGCGTTTCATCTTCGACCTGCTCG 1440 lyArgAspAlaThrArgValAsnAspLeuPheGlyThrGlnValArgGlnGlyGlyPheS
1441 GCCGCGACGCCACCCGCGTCAACGATCTATTTGGTACCCAGGTTCGCCAAGGCGGATTCT 1500 erLeuAlaAspAspAlaAsnPheGluLysAlaAlaAlaGluTyrGlyPheAlaSerGlyA
1501 CACTGGCTGATGACGCCAACTTTGAGAAGGCTGCAGCAGAATACGGTTTCGCCTCCGGAC 1560 rgSerThrHisAlaAspArgValAlaThrIleAlaAspValHisSerArgLeuAspValL
1561 GATCCACCCATGCTGACCGTGTGGCAACCATCGCTGACGTGCATTCCCGCCTCGACGTAC 1620 euIleAspProHisThrAlaAspGlyValHisValAlaArgGlnTrpArgAspGluValA
1621 TAATCGATCCCCACACCGCCGACGGCGTTCACGTGGCACGCCAGTGGAGGGACGAGGTCA 1680 snThrProIleIleValLeuGluThrAlaLeuProValLysPheAlaAspThrIleValG
1681 ACACCCCAATCATCGTCCTAGAAACTGCACTCCCAGTGAAATTTGCCGACACCATCGTCG 1740 luAlaIleGlyGluAlaProGlnThrProGluArgPheAlaAlaIleMetAspAlaProP
1741 AAGCAATTGGTGAAGCACCTCAAACTCCAGAGCGTTTCGCCGCGATCATGGATGCTCCAT 1800 heLysValSerAspLeuProAsnAspThrAspAlaValLysGlnTyrIleValAspAlaI
1801 TCAAGGTTTCCGACCTACCAAACGACACCGATGCAGTTAAGCAGTACATAGTCGATGCGA 1860
```

FIGURE 4C

```
        leAlaAsnThrSerValLys
1861    TTGCAAACACTTCCGTGAAGTAACTTGCTTTACGCCAAGGCCTGATTCCTCTCTTTATGG    1920

1921    GATGGAACCAGGCCTTTCGCATTGAGTGGCGTTTTAAGGCCTCCAATTCTTAGAACGGGT    1980
        - - - - - - - - - - - - - - - - - - - - - - -
        Computer predicted terminator structure, *+termination point

1981    GTTTGACATGGAGGGGTCACAGTCAAGCCGTTAGAAGCGATTCTGGGAGGGCAAGTTTTT    2040

2041    CGGAGTTGGAGGTCGAATTTCCGCTGAACTGATGGGAACCAGACAGGCGTGACAAGATTG    2100

2101    GCTAAAAACCTGAAGTTTTGTCACGCCTGTCTGGTTTCCCTCTTGTCGGTGCGAGCGAGT    2160

2161    CCCTTGAACGACACAGATCGCGCCAAATGGAAGTGTCTGCGACCCCAGAATATTTGATTC    2220

2221    CCCGGTCCGAGTCGTGCGAAAAATGCTCTGGTTAGTCCTCGATCATCGCAATCGCATCAA    2280

2281    TTTCCACAGTTGCACCATAAGGAAGCGATGATGCACCCACGAAAGAGCGTGCCGGGCGGC    2340

2341    CTTCGAGGAAATGCTCTCGGAATTGCTCGTTGCATTCTTCGCGCAGGCTGATGTCGGTGA    2400

2401    CAAAGTAAGTGAGTTTCACAACGTCTTTGAGTTCACCACCAGCGGTCGGAGGCGTTCACG    2460

2461    CATGCGTTCAAGTGCTGCATCAACTGCTTCTTTACGACCGACGACTGGTTGGTAGTCCTT    2520

2521    GTCTACTGAAAGAGCGCCGGAGACGAAGATGAAATTTCCGACGCGTTTTGCGGGGGACTT    2580

2581    ATGGGTGATCATTCGACATGTGGCCAACCATAGCTGTTTCCCCGAAGAGAGTGCCGGAAC    2640

2641    AGGCATTTTAGAGGTGGGGGAGCACTTCTTCGTAAATCTGGGTCAGTACTTCGCTTGCTG    2700

2701    GTCGGCGCTGGATGTTGAAGATGACGTGGTCGATGCCAAGTTCCGAAAGCGGTGGAGGTC    2760

2761    TTCGATGAGTTCCTGGCTGCCTACCTCTACGCCAGAGTGATTTCTTTGTGGGTGTTTCCT    2820

2821    TCGGTGAGGTTGAGCCCCATGGAGGAAATCAACAAGGGGCGGGTGCCACCACGGGCTTTG    2880

2881    TCCCAGAGATCGAGGCGTCCGACTTGAGCTTCAGCGGGGCGGTAGTAGGTTGCCCATCCG    2940

2941    TCGGCGTTTCGGGCGATCCATTGCACTGTTTGTCGGGCAGAACCTACAGCGATCATGGGG    3000
```

FIGURE 4D

3001 ATCTGAGCTTCAGGTGGCGTGGTTGGCGCAAATTCAAGGTCGGCCCGCATCGCAGGATCC 3060

3061 TTCGACAAAGCTGCACGCAAAATTGCCCACCCAGACTGAATATCAGCGCGTCGATTGTCT 3120

3121 AAGCTTTTCGGAAAAATCTCGAATTC 3146

FIGURE 5A

SmaI

```
CCCGGGTTGATATTAGATTTCATAAATATACTAAAAATCTTGAGAGTTTTTCCGTTGAAA
GGGCCCAACTATAATCTAAAGTATTTATATGATTTTTAGAACTCTCAAAAAGGCAACTTT
                                          DraI
                                          -35
ACTAAAAAGCTGGGAAGGTGAATCGAATTTCGGGGCTTTAAAGCAAAAATGAACAGCTTG
TGATTTTTCGACCCTTCCACTTAGCTTAAAGCCCCGAAATTTCGTTTTTACTTGTCGAAC
               mRNA start        hyphenated dyad symmetry
   -10     *---->               | |  \Met***      | |
GTCTATAGTGGCTAGGTACCCTTTTTGTTTTGGACACATGTAGGGTGGCCGAAACAAAGT
CAGATATCACCGATCCATGGGAAAAACAAAACCTGTGTACATCCCACCGGCTTTGTTTCA
                              predicted start of thrA translation
                                                  ThrSerAlaSerAla
AATAGGACAACAACGCTCGACCGCGATTATTTTGGAGAATCATGACCTCAGCATCTGCC
TTATCCTGTTGTTGCGAGCTGGCGCTAATAAAAACCTCTTAGTACTGGAGTCGTAGACGG
```

HindIII
ProSer..
CCAAGCTT
GGTTCGAA

FIGURE 5B

```
                      STOP
                 U
             G       A
     MET  U-        G
           A       G
           C-G
           A-U
           C-G
       A           G
           G-C
           G-C
           U G
           U-A
           U-A
           U-A
           G-C
           U-A
           U-A
           U-A
```

STRATEGY FOR hom-thrB PROMOTER DELETIONS

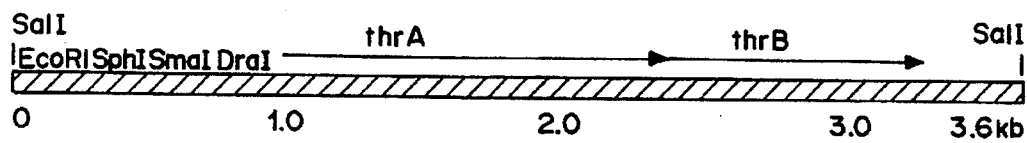

1.) determination of the approximate location of the thrAB promoter
- EcoRI, SphI, SmaI, or DraI restriction
- make blunt ends if necessary
- SalI restriction
- Isolate hom-thrB containing fragment
- ligate into pWST1 cut with SmaI and SalI 2.) fine deletion mapping of the thrAB promoter with Bal31
- SmaI restriction
- digest with Bal31
- SalI restriction
- Isolate hom-thrB containing fragment
- ligate into pWST1 cut with SmaI and SalI

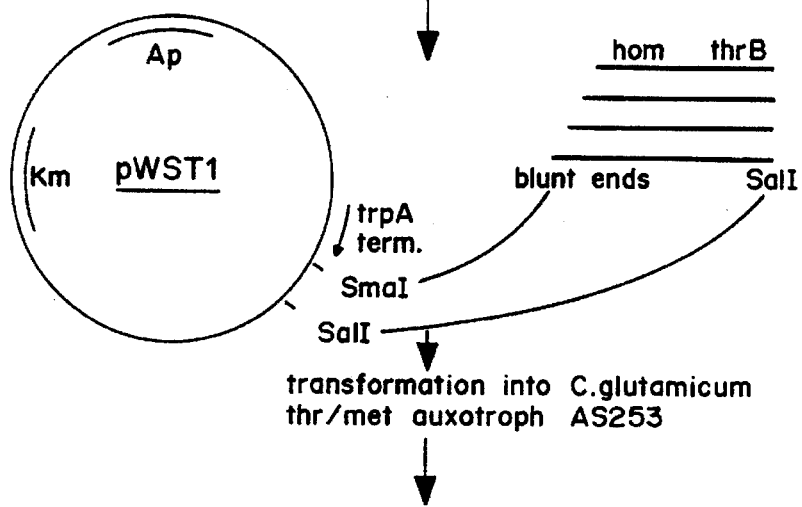

transformation into C. glutamicum thr/met auxotroph AS253 complementation analysis homoserine dehydrogenase enzyme assays determination of nucleotide sequences

*FIGURE 6*

GLUTAMICUM THREONINE BIOSYNTHETIC PATHWAY

This is a continuation of U.S. Ser. No. 07/062,552 filed Jun. 12, 1987 now abandoned.

BACKGROUND OF THE INVENTION

The present invention is generally in the field of genetic engineering, and specifically, in the area of manipulation of amino acid biosynthesis in Gram positive bacteria.

*Corynebacterium glutamicum* is a Gram positive, non-pathogenic microorganism that has long occupied a central role in the industrial production of amino acids by conventional fermentation processes. Past strain development has primarily depended on classical mutagenesis to remove competing pathways to thereby increase substrate availability, and to remove or reduce regulatory control of a particular biosynthetic pathway. Regulatory mutants were isolated by selecting strains resistant to toxic amino acid analogues. The use of chemical mutagenesis has been very successful and a number of economically viable L-amino acid fermentation strains, such as strain producing L-glutamate and L-lysine, have been established.

The recent development of cloning vectors, including those described in U.S. Pat. No. 4,649,119 to Sinskey et al., and methods for DNA transformation of *C. glutamicum*, as decribed by Katsumata et al., *J. Bacteriol.* 159, 306–311 (1984), and Yoshihama et al., *J. Bacteriol.* 162, 591–597 (1985), and the closely related *Corynebacterium (Brevibacterium) lactofermentum* described by Santamaria et al. in *J. Gen. Microbiol.* 130, 2237–2246 (1984), initiated a new era in the genetic manipulation of these organisms.

However, the commercial utilization of *C. glutamicum* recombinant DNA technologies for future strain development is dependent on the development of additional genetic tools and a better understanding of the fundamental molecular biology of this species. The use of recombinant DNA techniques to develop industrial strains would offer several advantages over classical mutagenic strategies. For example, specific alterations such as the replacement of a low efficiency promoter would be possible, the stepwise isolation of enhancing mutations could be avoided, regulatory systems could be engineered to allow the temporal control of gene expression during a fermentation process, and novel genes and/or pathways could be introduced into an organism.

It is therefore an object of the present invention to isolate and characterize genes encoding components of amino acid biosynthetic pathways in *Corynebacterium*.

It is another object of the present invention to clone the isolated amino acid biosynthetic genes, specifically those involved in the threonine biosynthetic pathway.

It is still another object of the present invention to elucidate the structure of these genes and the regulatory mechanisms that modulate their expression.

It is a further object of the present invention to characterize and modify the expression of the cloned, amino acid biosynthetic genes, as well as the primary structure and regulatory features of their protein products.

SUMMARY OF THE INVENTION

The present invention is a method for the isolation and characterization of *C. glutamicum* genes involved in amino acid biosynthesis, specifically, hom, thrB, and thrC, and sequences regulating their expression. Techniques for modifying their expression and regulation are also described. Methods and sequences facilitating further isolations and characterizations are also disclosed, including promoter probe vectors which are useful in screening for high efficiency and regulated promoters.

A *C. glutamicum* genomic library was constructed by cleaving chromosomal DNA with the restriction enzyme Mob1, inserting the resultant DNA fragments into a *C. glutamicum/Bacillus subtilis* shuttle vector, pHY416, and transforming the resulting recombinant molecules into *C. glutamicum*. Amino acid biosynthetic genes hom, thrB, and thrC, encoding homoserine dehydrogenase, homoserine kinase, and threonine synthase, respectively, were isolated by complementation of *C. glutamicum* auxotrophs. The hom-thrB genes were subcloned on a 3.6 kb Sal1 generated chromosomal fragment while thrC activity was isolated from a second recombinant plasmid within the genomic library and subcloned on a 2.7 kb Sph1 generated fragment. The hom-thrB and thrC loci were identified by a combination of enzyme assays and complementation of defined *E. coli* auxotrophs, and amino acid sequence homology.

Enzymatic assay of homoserine dehydrogenase activity, encoded by hom, in strains harboring the cloned gene demonstrated a 20-fold increase in specific activity compared to wild type controls. Both the chromosomal and plasmid encoded activities are strongly inhibited by L-threonine and repressed by L-methionine. The L-methionine repression of the plasmid encoded activity demonstrates that the structural gene and sequences responsible for its expression are included within the cloned fragment. Southern hybridization analysis demonstrated that the hom/thrB and thrC loci are separated by a minimum of 8.8 kb in the *C. glutamicum* chromosome. This is a different genomic organization from that observed in *E. coli* where the three genes represent a single operon. Three lines of evidence demonstrate that the *C. glutamicum* hom-thrB genes represent an operon. First, they are located together (separated by 11 base pairs) and coordinately regulated by L-methionine. Secondly, Northern hybridization analysis has identified a single 2.4 kb, L-methionine repressed RNA transcript, consistent with the size of the two coding regions. Finally, deletion of the promoter upstream of the hom gene significantly reduces the expression of both the hom and thrB genes.

The hom-thrB and thrC promoters were identified by complementation of auxotrophs, deletion analysis and S1 nuclease mapping. The hom-thrB operator, a hyphenated dyad symmetry element, was also identified by deletion analysis. Methods for modification, removal or replacement of these regulatory elements are described.

BRIEF DESCRIPTION OF THE DRAWINGS

FIG. 3 is the nucleotide sequence and predicted protein sequences of hom and thrB.

FIG. 4 is the nucleotide sequence and predicted protein sequence of the thrC gene.

FIG. 5a is the sequence of the *C. glutamicum* hom-thrB regulatory region indicating the mRNA initiation site, -35 and -10 regions of thrP1 and the hyphenated dyad symmetry element responsible for methionine mediated repression (thrO).

FIG. 5b is the potential stem/loop structure formed by the hyphenated dyad symmetry element.

FIG. 6 is a schematic of the construction of C. glutamicum hom-thrB promoter deletions and subsequent analysis.

DETAILED DESCRIPTION OF THE INVENTION

Recombinant DNA technology has been used to isolate, characterize and manipulate genes involved in the amino acid biosynthetic pathway of *Corynebacterium glutamicum*. The technology and results obtained aid in the elucidation of the fundamental molecular biology of *C. glutamicum* and construction of amino acid producing strains, particularly threonine.

Figure 1:
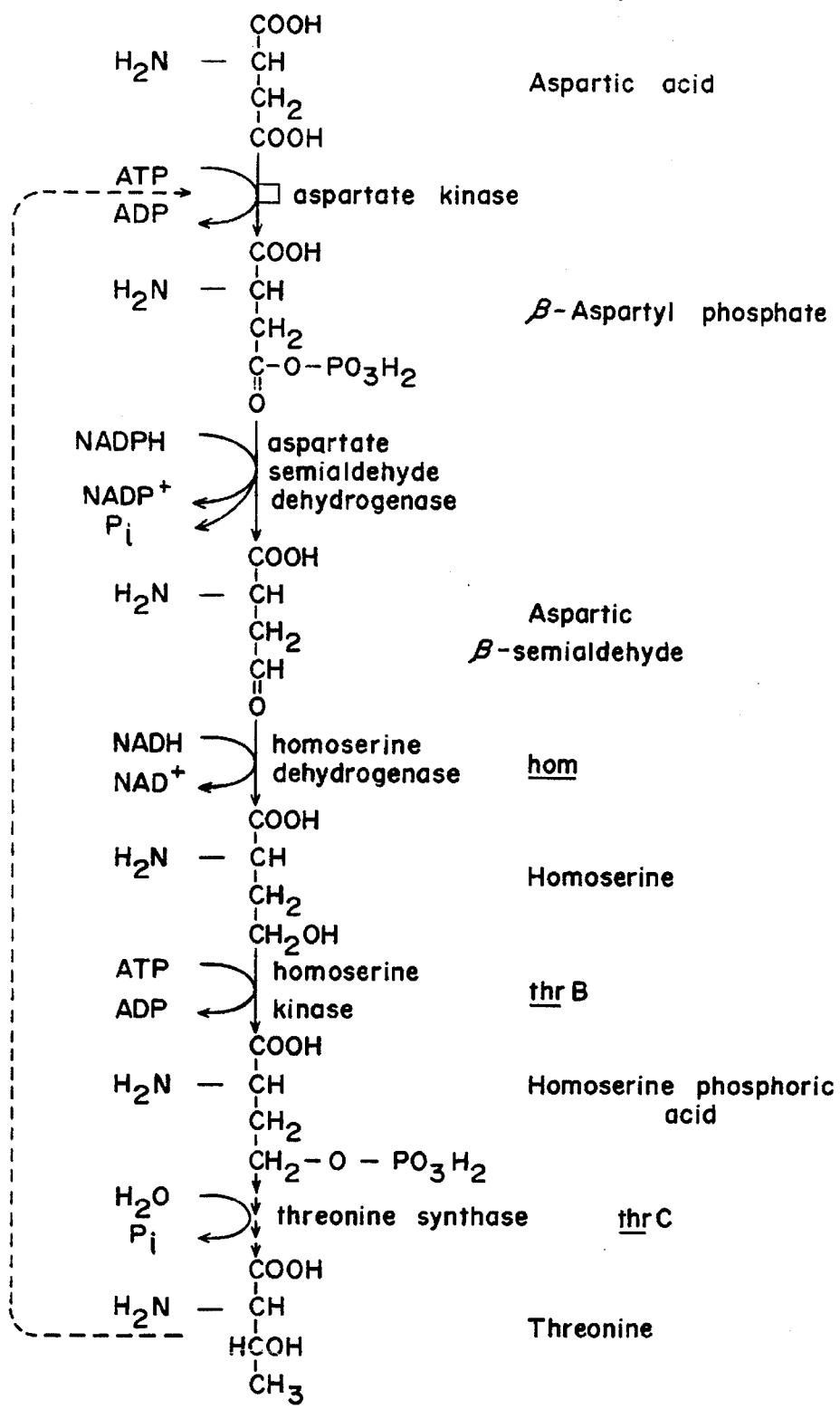
FIG. 1 is a schematic of the threonine biosynthetic pathway.

Threonine is produced in a series of reactions beginning with the reduction of the beta-carboxyl group of aspartic acid to the aldehyde, aspartic beta-semialdehyde, which takes place via an acyl phosphate intermediate, beta-aspartyl phosphate, in an ATP requiring reaction. Aspartic beta-semialdehyde is converted by homoserine dehydrogenase, encoded by hom, to homoserine. Homoserine is phosphorylated by homoserine kinase, encoded by thrB, to homoserine phosphate in an ATP requiring reaction. The product, homoserine phosphoric acid, is in turn converted to threonine by threonine synthase, encoded by thrC, a pyridoxal phosphate enzyme. Threonine, the end product of the sequence, is an inhibitory modulator of aspartate kinase. This reaction pathway is demonstrated in FIG. 1.

Genes encoding the three enzymes, homoserine dehydrogenase (hom), homoserine kinase (thrB), and threonine synthetase (thrC) have been isolated, identified, cloned, and their expression modified as follows. The cloning and determination of the nucleotide sequence of these genes provides a means for manipulating the expression and catalytic properties of the encoded enzymes. Means for altering the expression and the end product include in vitro mutagenesis of the *C. glutamicum* hom gene and selection of derivatives resistant to L-threonine mediated feedback inhibition, sequence determination of feedback resistant derivatives and the use of recombinant DNA techniques to combine separate genetic alterations, determination and modification of the promoter structure and protein start sites for hom, thrB, and thrC, increased expression of hom-thrB via increased promoter efficiency and removal of L-methionine transcriptional repression, and molecular joining of the *C. glutamicum* hom-thrB and thrC genes to form a hom-thrBC operon.

Isolation of thr- and thr-/met- auxotrophs of *C. glutamicum*.

A genetic background in which to isolate the threonine biosynthetic genes was constructed by mutating *C. glutamicum* and isolating auxotrophs defective in threonine biosynthesis. The *C. glutamicum* is maintained on LB media (10 g NaCl, 10 g Bactotryptone, 5 g Yeast extract, 1 l. $H_2O$) or minimal medium for *C. glutamicum* (MCG) (10 g glucose, 7 g $(NH_4)_2SO_4$, 3 g $K_2HPO_4$, 1 g $KH_2PO_4$, 0.4 g $MgSO_4 \cdot 7 H_2O$, 2 mg $FeSO_4 \cdot 7H_2O$, 2 mg $MnSO_4 \cdot H_2O$, 1 mg Biotin, 10 mg Thiamine, 2 ml trace elements, 1 l.$H_2O$). 1.4% agar was added for plates. The trace elements contained 44 mg $Na_2B_4O_7 \cdot 7H_2O$, 20 mg $(NH_4)_6Mo_7O_{27} \cdot 4H_2O$, 5 mg $ZnSO_4$, 135 mg $CuSO_4 \cdot 5H_2O$, 3.6 mg $MnCl_2 \cdot H_2O$, 435 mg $FeCl_3$ in 500 ml $H_2O$. Where appropriate, 50 g/ml L-threonine, 50 g/ml L-methionine, 50 g/ml ampicillin, 15 g/ml kanamycin or 10 g/ml rifampicin were added.

*C. glutamicum* AS019, a rifampicin resistant variant of ATCC 13059, was grown at 30° C. in LB to exponential phase ($2 \times 10^8$ cfu/ml), harvested by centrifugation and resuspended in an equal volume of minimal media for *C. glutamicum* (MCG). Cells were mutagenized by the addition of nitrosoguanidine (NTG) (40 micrograms/ml) to 1 ml of cells and incubation without shaking at 30° C. for 30 minutes. Mutagenized cells were harvested by centrifugation, resuspended in 1 ml LB media and diluted 1:100 into 10 ml aliquots of fresh LB. Following growth at 30° C. with shaking to stationary phase, the cells were diluted and plated on LB agar. Auxotrophs were screened by replica plating onto MCG plates and identification by growth patterns on amino acid pools. Only one strain displaying a particular auxotrophy such as threonine requirement was saved from each of the 10 ml aliquots.

Twenty four thr- and six thr⁻/met- *C. glutamicum* auxotrophs were isolated. The thr-met auxotrophs grow on MCG plates supplemented with homoserine. The thr- auxotrophs may have mutations in either of the threonine specific enzymes, homoserine kinase or threonine synthase. Transformation and complementation of the *C. glutamicum* auxotrophs.

Two threonine requiring auxotrophs of *C. glutamicum*, AS155 and AS178, were transformed using the following method. An overnight culture of AS019 was inoculated at a ratio of 1:100 into LB broth containing 0.2% glucose and 2.0% glycine. The cells were incubated at 30° C. for 15 hours with aeration. 10 ml of cells were harvested by centrifugation and washed in SMMC buffer (0.5/M Sorbitol, 20 mM $MgSO_4$, 20 mM $CaCl_2$, 50 mM Na Maleate, pH 7.0). Cells were resuspended in 2 ml SMMC buffer containing 2.5 mg lysozyme/ml. The cell suspension was incubated at 37° C. with shaking for 90 minutes. Cells were again harvested by centrifugation at 6000 rpm for ten minutes and resuspended in three ml SMMC buffer. 0.3 ml aliquots of "protoplasted" cells were placed in polypropylene tubes. Plamid DNA in 0.5M sorbitol was added. 0.7 ml of 40% PEG, molecular weight 3350, 50 mM Tris, 20 mM $CaCl_2$ pH 7.4 was added and gently mixed. 2.0 ml of SB broth (0.5M sorbitol, 1×LB, 20 mM $CaCl_2$, 20 mM $MgSO_4$) was added to the transformation mixture, which was then incubated at 30° C. without shaking for three hours. The *C. glutamicum* protoplasts obtained by growth in glycine and lysozyme treatment can also be suspended in SMMC and frozen at −80° C. for use in subsequent transformations.

The transformants were plated out on selected plates. The two threonine requiring auxotrophs AS155 and AS178 were transformed with a *C. glutamicum* genomic library containing approximately 2.5 genomic equivalents constructed in the *C. glutamicum/B. subtilis* chimeric plasmid pHY416, described by Yoshihama et al., *J. Bacteriol.* 162, 591–597 (1985) and Follettie and Sinskey in *J. Bacteriol.* 166 695–702 (1986). Kanamycin resistant transformants were selected and screened for complementation of the threonine auxotrophy by replica plating onto MCG/Km plates. Three AS155 transformants and a single AS178 transformant were capable of growth without threonine supplementation. Plasmids were isolated and characterized by restriction analysis.

Figure 2:
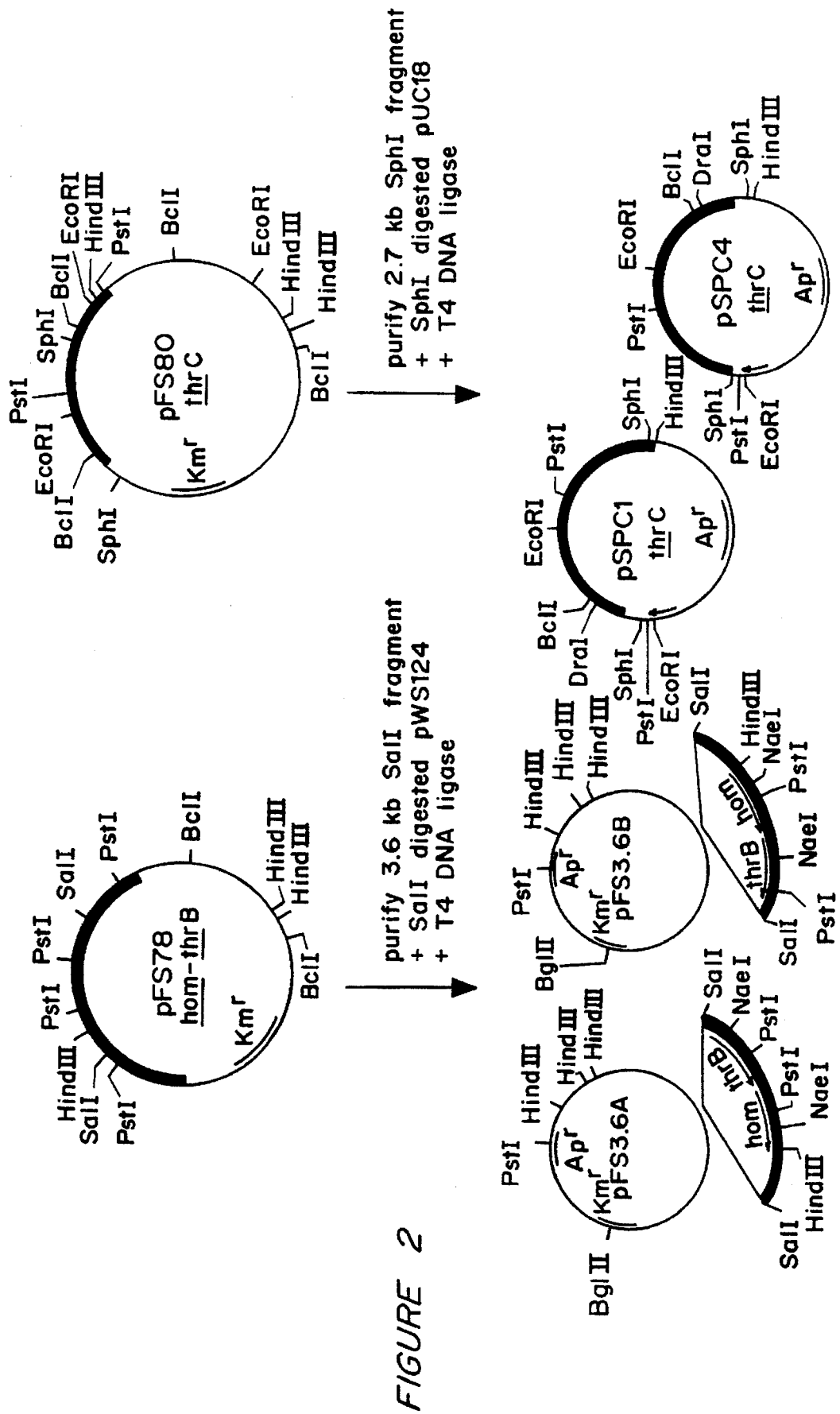
FIG. 2 is a graphic depiction of subcloning strategy and restriction maps of recombinant plasmids pFS78, pFS80, pFS3.6A, pFS3.6B, pSPC1 and pSPC4.

All four transformants harbored the same recombinant plasmid, designated pFS78, described in FIG. 2, which contain a 6.8 kb chromosomal DNA insert. The recombinant plasmid was transformed into 10 of the independently isolated *C. glutamicum* threonine auxotrophs and three auxotrophs requiring threonine and methionine or homoserine supplementation. The Km$^r$ transformants were screened for complementation on MCG/Km plates. The results demonstrated that pFS78 complements all three homoserine auxotrophs and four of the ten thr- auxotrophs, indicating that the plasmid carries the homoserine dehydrogenase gene, hom, as well as one of the threonine specific genes, thrB or thrC.

Two of the thr- auxotrophs not complemented by pFS78, AS148 and AS213, were transformed with the genomic library and Km$^r$ colonies screened for growth on MCG/Km plates. Both thr+ AS148 and thr+ AS213 transformants were obtained, and their plasmids isolated and characterized by restriction analysis. All thr+ transformants harbor the same 12.5 kb recombinant plasmid designated pFS80, also shown in FIG. 2, containing a 3.1 kb chromosomal DNA insert. The chromosomal sequence cloned in pFS80 complements four other thr- auxotrophs not complemented by pFS78. However, pFS80 was unable to complement the thr- or thr-/met- strains complemented by pFS78.

Subcloning and identification by enzyme assay, complementation of auxotrophs, and amino acid sequence homology of the *C. glutamicum* hom, thrB, and thrC locus.

Deletion analysis of pFS78 indicated that both the thr- and thr-/met- complementing activities are located on a 3.6 kb SalI generated chromosomal fragment. This fragment was purified by agarose gel electrophoresis and electroelution and ligated into the unique SalI restriction site of the *C. glutamicum/E. coli* chimeric vector pWS124, described by Batt, Shamnabruch and Sinskey, *Biotech. Letts.* 7:717 (1985). The recombinant vector, pFS3.6, complements both AS178 (thr-) and AS253 (thr-/met-). The plasmid also complements *E. coli* thrB auxotroph, *E. coli* 5076.

The 2.7 Kb SphI generated chromosomal fragment of pFS80 was purified by agarose gel electrophoresis and ligated into the unique SphI restriction site of pUC18. The resulting recombinant plasmids, designated pSPC1 and pSPC4, also diagrammed in FIG. 2, were able to complement *E. coli* 5077 (thrC) but not *E. coli* 5076 (thrB).

Southern hybridization analysis was used to determine the relationship of the hom-thrB and thrC loci. The results demonstrate that the hom-thrB and thrC locus in this species are physically separated by a minimum of 8.8 kb.

The homoserine dehydrogenase activity in crude extracts of wild type AS019 was compared to that of the homoserine auxotroph AS253 with and without the complementing plasmid pFS3.6 in order to determine the regulation and extent of overproduction of the cloned *C. glutamicum* hom gene product. Methods used for preparing a *C. glutamicum* crude extract preparation and assays for homoserine dehydrogenase, homoserine kinase and aspartokinase are as follows:

Homoserine dehydrogenase is measured by the decrease in absorbance at 340 nm due to the oxidation of NADPH (extinction coefficient=6220). The reaction mixture contains: 3 mM DL aspartate-beta-semialdehyde (ASA), 0.4 mM NADPH, 0.1M PO$_4$, pH 7.0, 0.5M KCl, and enzyme preparation, in a total volume of 0.7 ml. A blank reaction mixture without DL-ASA serves as a control. DL-ASA is synthesized by the ozonolysis of DL-allyl glycine according to the procedure of Black and Wright, *J. Biol. Chem.* 213, 39 (1955).

Homoserine kinase activity was determined by a coupled enzyme assay which measured the reaction product ADP. The reaction mixture contained 3.3 mM ATP, 0.45 MM NADH, 4.5 mM phophenol pyruvate, 1.0 mM L-homoserine, 10 mM MgCl$_2$, 12.5 units pyruvate kinase (Sigma, St. Louis, Mo.), 25 units lactate dehydrogenase (Sigma), 0.25M KCl, 100 mM HEPES buffer (pH 7.8) and enzyme preparation in a total volume of 1.0 ml. The reaction was monitored by the decrease in absorbance at 340 nm due to the oxidation of NADH. The absorbance decrease in the absence of added substrate, L-homoserine, was determined and subtracted from values obtained with the complete assay mixture.

Aspartate kinase activity, inhibited by threonine, is determined by measuring the aspartohydroxamate produced according to the procedure of Black and Wright, *J. Biol. Chem.* 213, 27 (1955). Protein in the crude extract is precipitated by adding 5 volumes of saturated ammonium sulfate and resuspended in 0.3 volume of buffer containing 0.1M Tris, pH 7.4, 0.2M KCl. The assay mixture contains: 0.1M Tris, pH 7.4, 10 mM ATP, 10 mM MgSO$_4$ 0.6M hydroxylamine (pH 7.4), 0.6M (NH$_4$)$_2$, 50 mM L-aspartate and enzyme preparation in a total volume of 1 ml. After 1 hr incubation at 37° C., the reaction was stopped by the addition of 1.5 ml of solution containing 10% FeCl$_3$.6 H$_2$O, 3.3% trichloroacetic acid and 0.7N HCl. After centrifugation, aspartohydroxamate concentration is measured by absorption at 540 nm (extinction coefficient=600). A blank reaction mixture without L-aspartic acid serves as a control.

Protein concentration of the crude extracts is determined using the Bio-Rad protein assay with bovine serum albumin standards (BioRad Laboratories, Richmond, Calif.).

The *C. glutamicum* thr-/met- strain AS253 harboring the parental vector pWS124 had less than 2.5% of the homoserine dehydrogenase activity present in the wild type AS019. Introduction of the cloned *C. glutamicum* hom gene present on pFS3.6A into *C. glutamicum* AS253 leads to a twenty-fold increase in the specific activity of homoserine dehydrogenase over that observed in wild type *C. glutamicum* AS019. The orientation of the cloned hom gene with respect to the vector affected its expression. Crude extracts of AS253 harboring pFS3.6B demonstrated an 11-fold increase in homoserine dehydrogenase activity relative to wild type.

The level of aspartokinase in *C. glutamicum* AS019 harboring either the parental vector pWS124 or the recombinant vector pFS3.6 was unchanged over that observed in the controls. Further, the aspartokinase specific activity was not repressed by growth in MCG supplemented with 2.7 mM L-methionine. The differential transcriptional control of homoserine dehydrogenase, in combination with the lack of increased aspartokinase activity in cells harboring pFS3.6 (hom-thrB), demonstrates that the two activities are not catalyzed by a bifunctional protein as in *E. coli*. The expression of the encoded homoserine dehydrogenase is repressed 3.2 fold by the addition of 2.7 mM L-methionine. Expression of the *C. glutamicum* thrA gene is also repressed by L-methionine, demonstrating that the expression of the pFS3.6 encoded hom gene is mediated by its native promoter/operator. Expression of the cloned *C. glutamicum* thrB gene was similarly repressed 2.6-fold by 2.7 mM L-methionine.

The activity of the homoserine dehydrogenase, both chromosomal and plasmid encoded, is inhibited by the addition of L-threonine to the assay mixture. Addition of 1 mM D-threonine or L-methionine does not affect the homoserine dehydrogenase activity.

The complete nucleotide sequence of 3704 bp is shown in FIG. 3 for hom and thrB. Two long open reading frames (ORF's) extend from position 907 to 2329 and from 2312 to 3269. The protein sequences of homoserine dehydrogenase and homoserine kinase are predicted on the basis of the sequence extending from the first potential translation initiation codon, either ATG or GTG (position 994) to the TAA stop at position 2330 for ORF1 and from the ATG at 2342 to the TAG stop 3269. The predicted proteins have molecular weights of 46,436 and 32,618 daltons for ORF1 and ORF2, respectively. A translation terminator is present at position 3279 to 3311, seven nucleotides downstream of the TAG stop codon. This is shown in further detail in FIG. 5. The sequence forms a strong step-loop structure having a stem length of 15 bp and a seven base loop similar to the rho-independent terminators from E. coli. The 5' sequence to ORF1 has a region strongly rich in A:T containing the hom-thrB promoter and site of action of the methionine mediated repression.

The DNA sequence of the chromosomal DNA insert in pFS80, encoding threonine synthase (thrC), was also determined by dideoxy sequencing techniques and is shown in FIG. 4. A restriction map was predicted and checked against restriction analysis results to corroborate the accuracy of the sequence data. Computer aided analysis (UWGCG Programs, UW Biotechnology Center, University of Wisconsin) was used to predict the thrC gene within the sequence data. These results were compared with in vivo genetic deletion analysis. An open reading frame extends 5' to GTG at 396) marking the amino terminal region of thrC.

The threonine synthase activity maps within the 1.57 kb Bcl1-Stu1 restriction fragment. The computer predicted structural gene sequence, GTG (396) to TAA (1881), lies completely within this fragment. The StuI restriction is 176 bp 3' of the preducted translation stop codon.

Heterospecific genetic complementation of the E. coli thrC 1001 auxotroph shows that the C. glutamicum thrC gene is expressed in E. coli. B comparison using computer searches for regions similar to E. coli ribosome binding sites and translation terminator sequences, a ribosome binding site adjacent to GTG(396) and a significant terminator-like sequence 35 bp 3' of the TAA at 1881 and well identified. Homology was detected between C. glutamicum and E. coli thrC regions at both DNA predicted protein sequence levels. Limited conservation of DNA sequence was observed between the E. coli thrC gene and the region 400 to 1400 bp of the C. glutamicum thrC sequence. There is consistent conservation in the central region (residues 100 to 350 of C. glutamicum thrC) and the carboxy terminal residues 430 to 480.

Identification of the hom-thrB transcription start site by S1 nuclease mapping and deletion analysis.

The transcriptional start site for the C. glutamicum hom-thrB genes was identified using S1 nuclease mapping, as described by Berk and Sharp, Cell 12, 721 (1977). The procedure requires the isolation and denaturation of a DNA fragment which overlaps the promoter and has been $^{32}P$ label at the 5'end of the antisense strand. Hybridization of this fragment to its cognate mRNA and subsequent digestion with the single strand specific exonuclease S1 results in the degradation of the 3'end of the labled DNA fragment up to the point at which it is protected by the RNA. The size of the resulting DNA fragment is determined by comigration with DNA fragments resulting from the sequencing reactions of Maxam and Gilbert, Methods in Enzymol. 65, 499–559 (1982). This enables the identification of the transcriptional start site. The results can then be confirmed by deletion analysis of the promoter using restriction enzymes and exonuclease Bal 31 to construct series of deletions which are then reinserted into the organism and assayed for activity.

The Sma1-HindIII restriction fragment that encompasses the hom-thrB promoter/operator and the first seven amino acid residues of the hom gene product was used in the S1 nuclease mapping studies. Plasmid pRA1 (pUC18 containing the 3.6 kb Sall C. glutamicum genomic fragment encoding hom-thrB) was cut with HindIII to generate a 1.014 kb restriction fragment, dephosphorylated with CIP (calf intestine phosphatase, Boehringer-Mannhein Biochemicals, Indianapolis, Ind.), labelled by treatment with polynucleotide kinase and gamma$^{32}$ P-ATP (specific activity greater than 5000 Ci/mmol, Amersham Corp. Arlington Heights, Ill.), subsequently cleaved with Sma1 (New England Biolabs, Beverly, Mass.) to produce a 242 bp DNA fragment that was then purified by preparative polyacrylamide gel electrophoresis. All manipulations were carried out in accordance with procedures described in *Molecular Cloning* by T. Maniatis et al. (Cold Spring Harbor Laboratory, Cold Spring Harbor, N.Y., 1982) and the enzyme suppliers recommendations.

Understanding the expression of a gene requires the isolation and structural characterization of the mRNA product, the size and number of transcripts, the regulatory control and the site of transcription initiation. Criteria evaluated for RNA isolated from *Corynebacteria* include RNA quality ($Abs_{260}$: $Abs_{280}$, ratio of about 1.95 to 2.05), purity (degradation and contamination determined by agarose gel electropheresis), and yield in mg RNA/liter cells ($Abs_{260}$=4 micrograms RNA/ml).

RNA was extracted from C. glutamicum AS019 using the guanidinium isothiocyanate/French press isolation method. In this method, a 1 l. LB culture of AS019 is grown at 30° C. to late exponential phase and harvested by 10 minutes centrifugation at 5000 RPM in a Sorvall GSA-250 rotor. The cells are washed at 4° C. in 0.1M NaCl, 10 mM Tris. Cl, pH 8.0, 1 mM EDTA, and harvested again. The pellets are combined in 50 ml 4M guanidinium isothiocyanate, 2-mercaptoethanol (GuT:2ME) and immediately lysed by compression through a French press at approximately 1500 psi. Cell debris is sedimented by centrifugation in a Sorvall SS-34 rotor for 10 minutes at 10,000 rpm. Six ml aliquots of the supernatant are applied to 4 ml of 5.7M CsCl, 10 mM EDTA, 25 mM sodium acetate and centrifuged at 34,000 rpm in a Beckman Ti50 fixed angle rotor for 24 hours.

The density gradient separates the sheared DNA molecules from the RNA, which forms a pellet at the tube base. This RNA pellet is resuspended in 5 ml 10 mM Tris, pH 7.5, 1 mM EDTA 5.0% Sarkosyl (TESK) containing 5.0% phenol. The solution is made 0.1M with 5M NaCl, and extracted with 10 ml 50% phenol, 49% chloroform, 1% isoamylalcohol (PCIA). The phases are separated by centrifugation in a Sorvall SS-34 at 3,000 rpm for 5 minutes and the phenolic phase back extracted with TESK containing 0.1M NaCl. The combined aqueous phases are made 0.2M with sodium acetate, pH 5.5, and the RNA precipitated overnight at −20° C. in 2.5 volumes of ethanol. After centrifugation at 10,000 rpm for 20 minutes at 4° C., the RNA pellet is washed in ethanol, dried under vacuum, and resuspended in RNase free water at a concentration of 0.5 mg/ml.

Total cellular RNA, isolated from AS019 grown in minimal media with and without L-methionine (400 microgram/ml) supplementation, was separated by agarose gel electrophoresis, transferred to nitrocellulose paper and probed either with pMF-L2 or pUC-B5. Plasmid pMF-L2 contains a 1.8 kb Nae1 fragment which spans both the hom and thrB genes but contains no flanking sequences. RNA is glyoxylated to prevent spurious electrophoretic patterns caused by potential secondary structure. For each lane, 20 micrograms of *C. glutamicum* RNA is suspended in 8 microliters of glyoxal reaction mixture (1M glyoxal, 50% DMSO, 10 mM potassium phosphate, pH 7.0) and incubated 1 hour at 50° C. Glyoxylated RNA samples are prepared for loading by the addition of 17 microliters formamide, 6.2 microliters formaldehyde, 3 microliters 10x running buffer 0.2M morpholinopropanesulfonic acid (MOPS), 50 mM sodium acetate, 10 mM EDTA) and 5 microliters loading dye (50% glycerol, 1 mM EDTA, 0.4% bromophenol blue, 0.4% xylene cyanol). Samples are loaded onto an agarose/formaldehyde gel (2.2% agarose, 1 x running buffer, 18% formaldehyde, pH adjusted to 7.0 with NaOH) and electrophoresed at 30 mA. HindIII restricted lambda DNA is labeled with $^{32}$P, denatured and glyoxylated similar to RNA samples and utilized as a molecular size standard. Following electrophoresis, nucleic acid is transferred to a nitrocellulose filter using the technique of Southern, *J. Mol. Biol.* 98, 503–517 (1975) except that no prior treatment of the gel was necessary. Following transfer for 15 hours, the filters are baked in vacuo at 80° C. for 2 hours.

The filters are prehybridized in sealed plastic bags for 16 hours at 42° C. in a minimum volume, approximately 10 mls of hybridization buffer (50% deionized formamide, 5×SSC, 50 mM sodium acetate, pH 6.5, 25 micrograms sonicated denatured salmon sperm DNA, 0.02% bovine serum albumin, 0.02% Ficoll, 0.02% polyvinyl pyrrolidone). (SCC=0.15M NaCl. 0.015M sodium citrate, pH 7.0). The DNA probe is labeled with 32p by nick translation, according to Rigby et al., *J. Mol. Biol.* 113, 237–251 (1977), heat denatured, added to the hybridization buffer, and incubated with the filter for 20 hour at 42° C. Filters are subsequently washed five times in 2×SSC/0.1% SDS at room temperature and then three times in 0.2 SSC at 50° C. After drying, the filters are exposed to X-ray film and specific bands of hybridization determined by autoradiography.

Hybridization of pMF-L2 to total *C. glutamicum* RNA leads to the appearance of a single 2.4 kb transcript. This observation is in agreement with the predicted size of the hom-thrB transcript (2408 base pairs), based on S1 nuclease mapping, and the computer predicted termination site of the thrB gene. The size of the observed transcript and the lack of a detectable second transcript hybridizing to the hom-thrB probe leads the conclusion that *C. glutamicum* expresses hom and thrB from a single transcriptional unit, representing the first defined operon in this organism. Results obtained by S1 nuclease mapping of the thrA-thrB junction support this conclusion.

Hybridization of hom-thrB specific RNA to the 242 bp SmaI-HindIII end-labeled probe was achieved by lyophilizing 30 micrograms *C. glutamicum* RNA with 10 ng probe DNA and resuspending in 10 microliters hybridization buffer (40 mM PIPES pH 6.4, 0.4M NaCl, mM EDTA, 80% deionized formamide). The DNA was denatured by heating at 90° C. for 10 minutes. Hybridization was performed overnight at 49° C.

The hybrid DNA-RNA molecules were digested with 2,000 units S1 nuclease (Bethesda Research Laboratories, Inc., Gaithersburg, Md.) in 235 microliters assay buffer (250 mM NaCl, 30 mM sodium acetate, 10 mM zinc sulphate, 200 microgram/ml calf thymus DNA). The digest was incubated at 37° C. for one hour and terminated by extraction with 250 microliters PCIA (phenal/chloroform/isoamyl alcohol, 50:48:2). Nucleic acids were precipitated from the aqueous phase with 0.2M sodium acetate, 2 micrograms yeast tRNA and 50 microliters ethanol at −20° C. Following centrifugation and drying, each sample was dissolved in 3 microliters formamide loading buffer (100 ml formamide, 0.72 g Na$_2$ EDTA, 0.03 g bromophenol blue) and applied to a 6% polyacrylamide/7M urea sequencing gel. The 242 bp SmaI-Hind111 restriction fragment was sequenced using the procedures for the G, C+T and C reactions as described in Maxam and Gilbert, *Methods in Enzymol.* 65, 499–559 (1982).

The SmaI-HindIII fragment labeled at the Hind111 5'terminus (antisense strand) acts as a specific probe to RNA complementary to this region. To detect the start of the hom-thrB mRNA transcript, total RNA is hybridized to the labeled probe and the unprotected single stranded nucleic acid digested with the single strand specific S1 nuclease. The length of the protected region of the DNA probe is resolved on a denaturing 6% polyacrylamide gel. The hom-thrB transcript initiates at coordinate 906, at the first of a GG doublet. This nucleotide is 88 bp 5' of the first available ATG codon in the hom open reading frame. This defines the promoter region responsible for hom-thrB expression and is designated thrP1 for threonine promoter 1. The sequence is shown in FIG. 5a.

There was no detectable degradation of the DNA probe from the 0.46 kb Fok1-PvuII restriction fragments spanning the hom thrB PvuII junction, indicating that the majority of the thrB expression was mediated by thrP1.

Identification and deletion of the operator mediating L-methionine repression of hom-thrB expression.

In addition to promoter identification, restriction and/or exonuclease Bal31 deletions have been utilized in identification and deletion of the operator (thrO), which mediates the L-methionine repression of hom-thrB expression and in the construction of a feedback inhibition deficient variant of the hom gene. These studies were facilitated by construction of a special vector designated pWST1. When investigating promoter structure and function on a plasmid, it is desirable to eliminate read through transcription from upstream promoters located within the cloning vector. Plasmid pWST1 contains the *E. coli* trpA terminator followed by a polylinker to facilitate the cloning of the gene in the various deletion generated variants. The effect of the deletions can be assayed in the absence of influence by upstream promoters. This vector is applicable not only to the analysis of the hom-thrB genes, but also the characterizations of other promoter/operator systems in *C. glutamicum*. pWST1 is constructed using the trpA terminator obtained from Pharmacia Fine Chemicals, Piscataway, N.J. Sac1 linkers are attached and the trpA terminator inserted into the polylinker region of M13mp19. The constructs are sequenced using the method of Sanger et al. *Proc. Natl. Acad. Sci. USA* 74, 5463–5467 (1977), to screen for insertion of the terminator in the proper orientation. The terminator/polylinker is subsequently ligated into the SmaI-SalI restricted pTF33, a derivative of the *C. glutamicum/E. coli* shuttle vector pWS124, described by Batt et al., *Biotechnol. Letts.* 7:717 (1985). DNA linkers and enzymes are obtained from New England Biolabs or Boehringer-Mannheim, as noted earlier.

The hom-thrB genes were ligated into SmaI/SalI restricted pWST1 on a 2911 bp SmaI-SalI restriction fragment and a 2,815 bp Dra1-Sal1 restriction fragment, designated pWFS2.9 and pWFS2.8, respectively. Further deletion of the hom-thrB upstream region is accomplished as diagramed in FIG. 6. The recombinant vector pWFS2.9 was linearized by Sma1 digestion and deletions constructed by digestion of 6 micrograms of DNA with the exonuclease Bal31 (0.2 units)/micrograms DNA. Aliquots of the reaction mixture were removed at 30 second intervals between 4 and 15 minutes, and the reaction stopped by dilution into one volume of 50 mM EDTA. The DNA was digested with Sal1 and the resulting hom-thrB containing fragments purified by agarose gel electrophoresis. These fragments were ligated into Sma1-Sal1 digested pWST1 and the resulting recombinant mixture used to transform C. glutamicum AS253 (hom).

Figure 7:
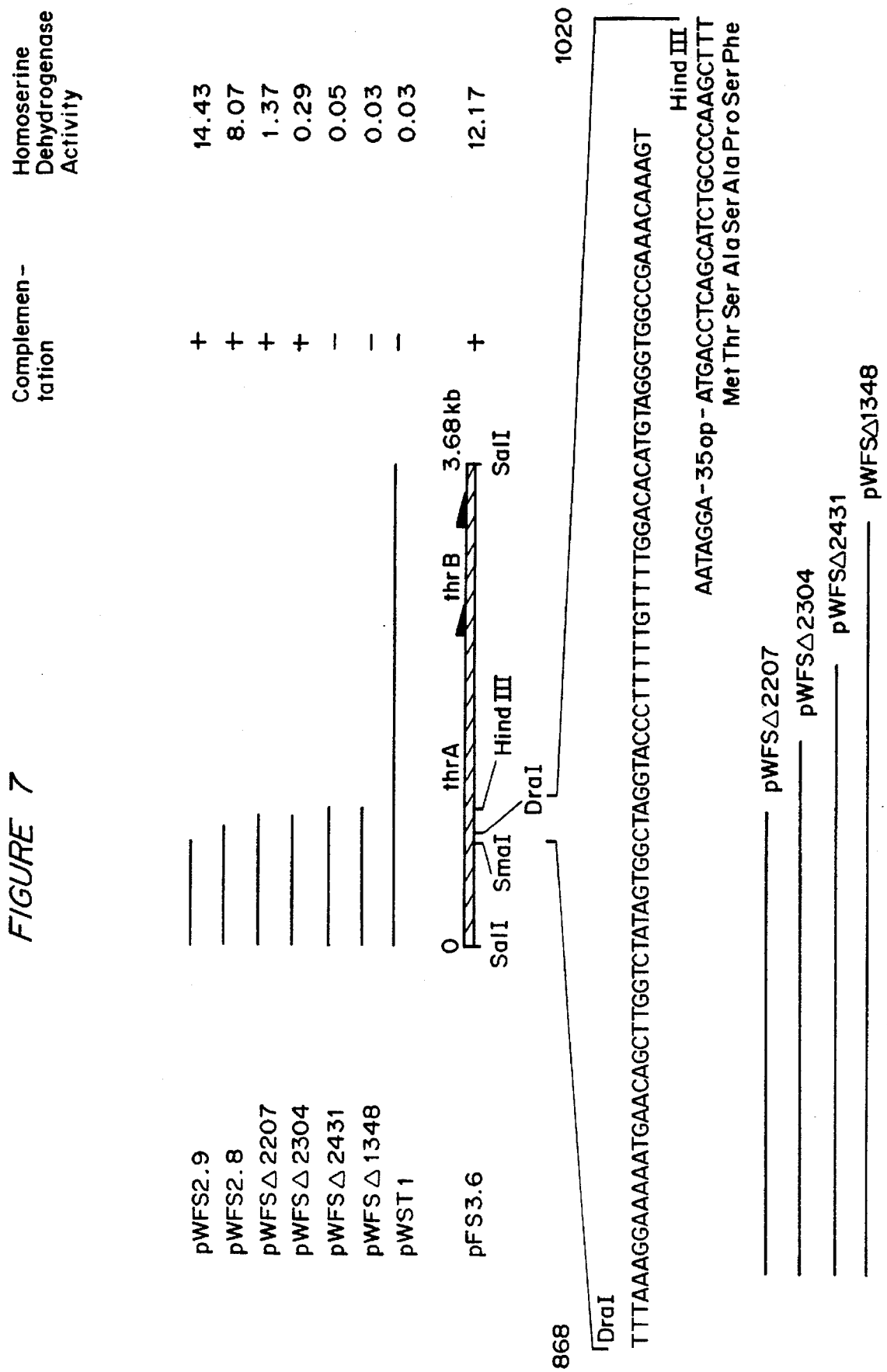
FIG. 7: Deletional analysis of the hom-thrB promoter region. The 3.6 kb *C. glutamicum* chromosomal DNA insert of pFS3.6 carrying the hom-thrB genes is indicated as a hatched box and the nucleotide sequence of the relevant promoter-containing DraI-HindIII fragment is shown. The extent of Bal31 generated deletions in various plasmid constructs based on vector pWST1 are presented as black bars. The start of transcription as determined by S1 nuclease mapping is indicated by an arrow.

The extent of the Bal31 generated deletions, diagrammed in FIG. 7, in complementing a non-complementing derivative plasmid is determined by nucleotide sequence analysis and measurement of the levels of homoserine dehydrogenase activity in crude extracts. The ability of the deletion plasmids to complement the hom-thrB auxotrophy of strain AS253 was checked by streaking the corresponding AS253 transformants onto MCG/kanamycin agar plates.

The results of the deletion construction and their effect on hom gene expression show that deletion of sequences upstream of hom, up to the Sma1 (pWFS2.9) or Dra1 (pWFS2.8) restriction site (218 and 124 bp prior to the predicted translational start site, respectively) does not drastically influence the expression of the hom gene.

As predicted from the S1 nuclease studies, the Dra1-Sal1 hom-thrB fragment contains both the -10 and -35 regions which are critical for promoter activity in E. coli, as reported by Hawley and McClure, Nucleic Acid Res. 11:2232 (1983). Further deletion by Bal31 markedly reduces the expression of the hom gene product homoserine dehydrogenase, supporting the data obtained with S1 nuclease mapping of thrP1. Two of the deletion derivatives, pWFSdelta2304 and pWFSdelta2207 are able to complement C. glutamicum AS253 despite the reduction in hom expression to 2 and 10%, respectively, of that observed in strains containing the parental plasmid pFS3.6. The relative specific activity of homoserine dehydrogenase observed in C. glutamicum AS253 (hom) harboring these two deletion derivatives is 3.1 and 0.7 with respect to that observed in wild type strains. C. glutamicum auxotrophs requiring threonine/methionine express approximately 2% of the wild type level of homoserine dehydrogenase activity. The deletion of the hom promoter carried in pWFSdelta2431 results in a 96-fold decrease in the expression of the cloned thrB gene thus demonstrating a common promoter.

The Bal31 generated deletions enable the mapping of the boundary between those deletion derivatives which complement the threonine/methionine auxotrophy and those that fail to complement, between 63 base pairs (pWFSdelta2304) and 56 base pairs (pWFSdelta2431) upstream of the predicted hom translation start sites. The observation that deletions extending to locations beyond the putative start point of transcription (88 bp upstream of the hom start codon) is determined by S1 nuclease mapping, does not necessarily result in the complete loss of homoserine dehydrogenase activity. This loss may also be due to weak promoter activity adjacent to the main transcription start site.

The mechanism of transcriptional regulation of the hom-thrB operon was determined to involve control by the single stem/loop attenuator shown in FIG. 5. Specific deletion of the stem/loop structure removes the methionine repression of hom-thrB expression. In this structure, the sequence ATGTAG, encoding Met-Stop, forms the loop. The sequence TTTTGGACA, similar to the TTGGAGA that precedes the predicted translational start site of the hom gene, precedes the ATG and thus represents a potential ribosome binding site. A possible model is one in which a bound ribosome can be momentarily stalled due to a low concentration of charged methionine tRNA, thus preventing stem/loop formation and allowing transcription to continue. At higher concentrations of methionine, the ribosome would move to the TAG Stop signal and disengage, allowing stem/loop formation.

LacZ protein fusions can be used to evaluate promoter and operator functions directly in C. glutamicum. This method is demonstrated using the hom-thrB promoter/operator, isolated on a 330 bP Sma1-Hind111 fragment purified and ligated into similarly digested pSKS107 that contains a promoterless lactose operon. The construction creates a hom-lacZ protein fusion containing the N-terminal eight hom amino acid residues preceding the lacZ gene product beta-galactosidase. The expression of the fusion protein products required the insertion of a ribosome binding site, initiating codon (ATG/GTG), under the control of the hom-thrB promoter/operator. The recombinant vector was introduced into E. coli JM83 where beta-galactosidase activity as observed in crude extracts. Supplementation of the growth medium with L-methionine represses the expression of lacZ two-fold.

Deletion of a portion of the dyad symmetry element required for operator function demonstrates the role of the dyad symmetry element in the regulation of the hom-thrB gene. A 1.48 kb Kpn1 restriction fragment containing the hom gene of the Bal31 deletion derivative, pWFSdelta2207 was purified and used to replace its counterpart in the parental vector pFS3.6A. The resulting recombinant plasmid, designated pWFS2207delta1, contains a specific 10 base pair deletion removing the left half of the dyad symmetry element. Identical levels of homoserine dehydrogenase activity were measured in strains grown in MCG medium with and without methionine supplementation. This demonstrates that the dyad symmetry element is the site of L-methionine repression (thrO).

Identification of the thrC promoter by deletion analysis, complementation of auxotrophs and overproduction of the enzyme.

The promoter sequence for expression of thrC was also determined by deletion analysis, auxotrophic complementation, and overproduction of enzyme.

The overproduction of the product of the thrC gene, threonine synthetase, can be measured from crude extracts of C. glutamicum strains AS213 and wild type AS019 containing the parental vector pHY416 or the thrC containing pFS80. The two strains containing the plasmids are grown in MCG medium, the cells harvested, lysed, cell debris removed by centrifugation, the protein purified by 40 to 60% ammonium sulphate fractionation, DEAE-Sephadex column chromatography with a 0.2M to 0.2M to 0.6M KCl gradient, and anion exchange chromatography in a FPLC column diluted with a 0.1M to 0.7M KCl gradient. The results demonstrate that the protein is produced at a level 200% of that observed in the wild type. The method produces threonine synthetase specific activity demonstrating a purification of over 350-fold. The protein has a molecular weight of 56,000 by SDS polyacrylamide gel electrophoresis.

Analysis of activity complementation of the thrC auxotroph indicates that the promoter for the thrC gene sequence precedes the predicted translation start site for the thrC gene product by approximately 80 base pairs. The sequence, TTGAAA - - - (16 bp) - - - TAGGGT, is closely related to the E. coli consensus sequence as well as the promoter sequence determined for C. glutamicum thrP1, AAAGCA - - - 18bp - - - TATAGT. Confirmation of the identification of the sequences the thrC gene promoter sequence is done by S1 nuclease analysis.

Modification of the enzyme structure and expression of hom, thrB and thrC.

Once the hom, thrB and thrC genes are identified, including the identification if the initiation sites of both mRNA and protein synthesis for the genes, it is possible to increase the quantity of gene expression by increasing the gene dosage by localization of specific genes on a multicopy plasmid, by site-directed mutagenesis or replacement of the promoter, by increasing translational efficiency through alteration of the ribosome binding site, or by increasing stability of the protein by site-directed mutagenesis. The quality of the particular gene can be increased using in vitro and site-directed mutagenesis to alter substrate utilization as well as the kinetic and regulatory properties of the enzyme. Physical properties such as heat stability can also be modified. The construction of a vector with the three genes transcribed as a single unit under the control of a high efficiency promoter results in more efficient threonine synthesis. One can also remove the L-threonine feedback inhibition of homoserine dehydrogenase or the threonine and lysine inhibition of aspartokinase to produce the overproduction of threonine. The feedback inhibition of homoserine dehydrogenase can be removed by in vitro mutagenesis using either hydroxylamine and/or sodium bisulfite, methods well known to those skilled in the art, or by recombinant techniques. The mutagenized plasmids are reintroduced into *C. glutamicum* and screened for AHV resistance or by enzyme assays. Increased promoter efficiency can also be accomplished by site directed mutagenesis of the existing promoter or by replacement with a high efficiency promoter.

The thrC gene can be placed under the transcriptional control of high efficiency promoters such as the *E. coli* promoter tac to produce elevated levels of the gene product. The expression vector pKK233-2, obtained from Pharmacia Fine Chemicals, is restricted with Nco1-HindIII. The plasmid pFS80 is cleaved with Bcl1, blunt ended with Klenow polymerase, and Nco1 linkers ligated onto the flush ends. The ligation product is double digested with Nco1 and HindIII, a 2.8 kb fragment purified and ligated into similarly digested pKK233-2. The resulting recombinant vector designated pKC14 is transformed into *E. coli* JM105. The requirement for IPTG (isopropyl-beta-D-thiogalactopyranoside) induction demonstrates that the thrC gene is under the transcriptional control of the tac promoter. The threonine synthetase activity measured in the absence of IPTG was 1.3 nmole/min/mg protein. The addition of 2 mM IPTG induces 24 times the threonine synthetase (30.9 nmole/min/mg-protein).

The homoserine dehydrogenase and homoserine kinase polypeptides encoded by the open reading frames corresponding to the hom and thrB gene products can be expressed and purified for analysis. The enzymes are purified from 10 liters of MCG broth from a CHEFLAP fermentator innoculated with a 300 ml overnight culture of *C. glutamicum* AS019/pFS3.6 grown for 24 hours at 30° C. with 470 rpm agitation. Cells were harvested by ultrafiltration and centrifugation, the cell pellet resuspended in lysis buffer (100 mM $KPO_4$, pH 7.0, 0.5M KCl) and the cells lysed by repeated passage through a French pressure cell. Debris is removed by centrifugation, the supernatant precipitated with ammonium sulphate, and the enzyme activities separated on a DEAE-Sephadex A-50 column eluted with a linear 0.3M to 0.8M KCl gradient. Fractions containing the appropriate enzyme activity are pooled and the proteins analyzed by SDS polyacrylamide electrophoresis. The proteins are then further purified on hydroxylapatite HPLC prior to final separation by preprative SDS-PAGE. The purified homoserine dehydrogenase remained active through the procedure and has a final molecular weight of 47,000 daltons. The activity of the homoserine kinase is lost, but the protein had a molecular weight of 32,000.

The observed molecular weights are in close agreement with the molecular weights predicted from the nucleotide sequences. The $NH_2$ terminus of the homoserine dehydrogenase is blocked, however, the amino acid composition is in good agreement with the amino acid composition predicted from the gene sequence. The expression of activity by ligation of the Sma1-Hind111 fragment containing the *C. glutamicum* thrP1 and predicted $NH_2$-terminal seven amino acid residues of the hom gene product indicate that the N-terminal sequence is correct. The first ten residues of the thrB gene product, homoserine kinase, is in complete agreement with the predicted amino acid sequence. This identifies the translation initiation site for the thrB gene as the ATG at nucleotide 2342, confirming the predicted primary structure of the *C. glutamicum* homoserine kinase. The protein appears to undergo post-translational removal of the N-formyl-MET, a relatively common feature of procaryotic proteins.

Construction and application of a C. glutamicum promoter probe.

A promoter probe for use in identifying, isolating, and quantifying the efficiency of promoters is based on pWST1 and designated pAL-1. The chloramphenicol acetyltransferase (CAT) gene is used as the promoter probe gene. The cat gene is expressed in *E. coli.*, *B.subtilis*, and *C. glutamicum*. Since cloning of strong promoters can induce plasmid instability by transcriptional interference at the replication origin, it may be necessary to clone the fd enteric bacteriophage major gene terminator at the 3' terminus of the test gene. Potential promoter sequences can then be screened for the acquisition of chloramphenicol resistance. Preliminary estimation of promoter efficiency can be accomplished by determining the extent of antibiotic resistance.

A number of promoter sources can be screened for their efficiency in *C. glutamicum*. High efficiency promoters from other procaryotic systems are known, for example, *E. coli* trp, the hybrid Ptac, lambda pH, and *B. subtilis* Preg. Random *C. glutamicum* chromosomal DNA and/or corynephage DNA fragments can also be inserted into the polylinker site, upstream in the test gene and cat activity determined to assess promoter efficiency. DNA sequencing and determination of the transcriptional start sites are used to characterize the promoter structure. For example, the 266 bp DraI-HaeIII fragment which spans the predicted thrC promoter region was purified and ligated into the Sma1 restriction site of the pAL-1 polylinker. The resulting recombinant mixture was introduced into *E. coli* and chloramphenicol resistant transformance obtained.

The primary site of metabolic regulation of threonine biosynthesis in *C. glutamicum* is the L-threonine inhibition of homoserine dehydrogenase. To remove the metabolic block, in vitro mutagenesis has been used to alter the hom gene product to produce feedback inhibition deficient variants. The recombinant plasmid pWFSdelta2207 was used as a source of the hom gene. This plasmid expresses a lower level of homoserine dehydrogenase (10%) than pFS3.6A, eliminating potential artifacts due to the overproduction of the hom gene product. Plasmid DNA was digested with Kpn1, separated by agarose gel electrophoresis and the fragments isolated by electroelution into dialysis bags. The 1.43 kb Kpn1 fragment containing the hom gene was purified and treated with hydroxylamine. This is a potent mutagen primarily causing AT to GC and GC to AT transitions. The mutated hom gene was isolated and 3 micrograms of target DNA resuspended in 280 microliters of 1M hydroxylamine, 0.3M $KPO_4$, pH 6.0, aliquots removed at between 10 and 300 minutes and the reaction stopped by ethanol precipitation. The mutagenized fragments were religated to the large, 12.7 kb, Kpn1 restriction fragment and transformed into *E. coli* JM83.

Plasmid DNA from ampicillin resistant transformants was purified on CsCl gradients and transformed into the restriction deficient *C. glutamicum* AS019-E12. These transformants were then screened for resistance to alpha-aminohydroxyvaleric acid (AHV) in order to select for a deregulated hom gene product. Homoserine dehydrogenase activity assays were used to confirm and demonstrate the removal of the L-threonine mediated feedback inhibition. Different mutations could be combined by recombinant DNA techniques to determine the extent to which they are cooperative.

The present invention, nucleotide sequences encoding threonine biosynthetic enzymes, and methods and sequences for the expression and regulation of expression of these enzyme encoding sequences are disclosed. Modifications and variations of this invention will be obvious to those skilled in the art of genetic engineering from the foregoing detailed description. It is intended that these modifications and variations will fall within the scopes of the appended claims.

We claim:

1. A method for making an expression vector for the production of threonine in a bacteria comprising:

inserting isolated nucleotide molecules comprising the genes encoding homoserine dehydrogenase, homoserine kinase, and threonine synthase in the threonine biosynthetic pathway of Corynebacteria with one or more selected nucleotide regulatory molecules capable of mediating the expression and regulation of the enzyme encoding molecules, wherein these regulatory molecules are selected from the group consisting of a promoter molecule having the sequence TTTAAAGCAAAAATGAACAGCTTGGT CTATAGTGGCTAG for regulation of the homoserine dehydrogenase gene and homoserine kinase gene, a promoter molecule having a higher transcriptional efficiency than the promoter molecule having the sequence TTTAAAGCAAAAATGAACAG CTTGGTCTATAGTGGCTAG for regulation of the homoserine dehydrogenase gene and homoserine kinase gene, a ribosome binding site having the sequence TTGGAGA for regulation of the homoserine dehydrogenase gene and homoserine kinase gene, a ribosome binding site having a sequence having higher transcriptional efficiency than the ribosome binding site having the sequence TTGGAGA for regulation of the homoserine dehydrogenase gene and homoserine kinase gene, a transcription termination molecule having the sequence AAGGAAGGCCCCTTC GAATCAAGAAGGGGCCTT for regulation of the homoserine kinase gene, a transcription termination molecule having the sequence GATGGAACCAGGCCT TTCGCATTGAGTGGCGTTTTAAGGCCTCCA for regulation of the threonine synthase gene, a transcriptional regulatory molecule having the sequence TTTG TTTTGGACACATGTAGGGTGGCCGAAACAAA for regulation of the homoserine dehydrogenase gene, and a repressor molecule, into an expression vector for expression in a bacterial host capable of expressing said nucleotide molecules.

2. The method of claim 1 further comprising inserting said expression vector into a host capable of expressing said nucleotide molecules.

3. The method of claim 2 wherein said expression host is *Corynebacterium*.

4. The method of claim 1 wherein said regulatory molecule is a promoter having higher transcriptional efficiency than the promoter having the sequence TTTAAAGCAAAAATGAACAGCTTGGT CTATAGTGGCTAG for regulation of the homoserine dehydrogenase gene and homoserine kinase gene, wherein said higher efficiency promoter is a mutant of the promoter molecule having the sequence TTTA AAGCAAAAATGAACAGCTTGGTCTATAGTG GCTAG.

5. The method of claim 1 wherein said regulatory molecule is a promoter having a higher transcriptional efficiency than the promoter having the sequence TTTAAAGCAAAAATGAACAG CTTGGTCTATAGTGGCTAG for regulation of the homoserine dehydrogenase gene and homoserine kinase gene, wherein said high efficiency promoter is selected from the group consisting of *Escherichia*, *Bacillus*, *Staphylococcus* and *Streptococcus* promoters.

6. The method of claim 1 further comprising selecting a multicopy plasmid as the expression vector.

7. The method of claim 1 further comprising mutating said enzyme encoding nucleotide molecules and selecting for increased temperature stability of the enzyme.

8. The method of claim 1 further comprising mutating said enzyme encoding nucleotide molecules and selecting for improved substrate utilization.

9. The method of claim 1 wherein said enzyme encoding and regulatory molecules include an operator further comprising modifying said operator to enhance expression of the genes.

10. The method of claim 9 wherein said modification is a deletion of a portion of a dyad symmetry element required for operator function.

11. The method of claim 9 wherein said operator is mutated.

12. The method of claim 9 wherein said operator is replaced with a operator other than the operator associated with the chromosomal gene encoding said enzyme.

13. An isolated DNA molecule comprising a *Corynebacterium* promoter and a ribosome binding site TTGGAGA.

14. An isolated *Corynebacterium* DNA transcription termination molecule having a sequence comprising

AAGGAAGGCCCCTTCGAATCAAG

AAGGGGCCTT.

15. An isolated *Corynebacterium* DNA transcription termination molecule having a sequence comprising

GATGGAACCAGGCCTTTCGCATT

GAGTGGCGTTTTAAGGCCTCCA.

16. An isolated *Corynebacterium* DNA molecule capable of repressing translation in the presence of excess methionine wherein the molecule has a sequence comprising TTTGTTTTGGACAC<u>ATG</u>TTC<u>TAG</u>GGTGGCCGAAACAAA.
              met     stop

* * * * *